US008170310B2

(12) United States Patent
Woo

(10) Patent No.: US 8,170,310 B2
(45) Date of Patent: May 1, 2012

(54) AUTOMATIC OUTCOME ANALYSIS USING RADIOLOGICAL IMAGES

(75) Inventor: Yijin Woo, Barrington, IL (US)

(73) Assignee: General Electric Company, Schenectady, NY (US)

( * ) Notice: Subject to any disclaimer, the term of this patent is extended or adjusted under 35 U.S.C. 154(b) by 579 days.

(21) Appl. No.: 12/390,738

(22) Filed: Feb. 23, 2009

(65) Prior Publication Data
US 2010/0215232 A1 Aug. 26, 2010

(51) Int. Cl.
*G06K 9/00* (2006.01)
*G06K 9/54* (2006.01)
(52) U.S. Cl. .......................... 382/128; 382/131; 382/132
(58) Field of Classification Search .................. 382/128, 382/131, 132, 218
See application file for complete search history.

(56) References Cited

U.S. PATENT DOCUMENTS

| | | | | |
|---|---|---|---|---|
| 5,974,201 | A * | 10/1999 | Chang et al. | 382/305 |
| 6,128,400 | A * | 10/2000 | Le Beux et al. | 382/132 |
| 7,587,075 | B1 * | 9/2009 | Stefan et al. | 382/128 |
| 8,000,777 | B2 * | 8/2011 | Jaeb et al. | 600/476 |
| 2002/0181752 | A1 * | 12/2002 | Wallo et al. | 382/130 |
| 2003/0081837 | A1 * | 5/2003 | Williame et al. | 382/215 |
| 2004/0015070 | A1 * | 1/2004 | Liang et al. | 600/407 |
| 2004/0120606 | A1 * | 6/2004 | Fredlund | 382/305 |
| 2005/0065421 | A1 * | 3/2005 | Burckhardt | 600/407 |
| 2007/0081707 | A1 * | 4/2007 | Sirohey et al. | 382/128 |
| 2007/0116334 | A1 * | 5/2007 | Fidrich et al. | 382/128 |
| 2007/0173702 | A1 * | 7/2007 | Dlugos et al. | 600/300 |
| 2008/0292152 | A1 * | 11/2008 | Nekrich | 382/128 |
| 2009/0143788 | A1 * | 6/2009 | Fang et al. | 606/130 |
| 2009/0279756 | A1 * | 11/2009 | Gindele et al. | 382/128 |
| 2010/0215232 | A1 * | 8/2010 | Woo | 382/131 |
| 2010/0254584 | A1 * | 10/2010 | Gulsun et al. | 382/131 |

* cited by examiner

*Primary Examiner* — John Lee
(74) *Attorney, Agent, or Firm* — McAndrews, Held & Malloy, Ltd.; Armando Pastrana, Jr.

(57) ABSTRACT

Certain embodiments of the present invention provide a system for analyzing a treatment of a patent including: an interactive image editor for allowing a user to interact with a first set image data corresponding to a pre-treatment radiological study of a patient, the first set of image data including an untreated clinical area of interest, such that the user is capable of interacting with the first set of image data to form a target outcome image for the clinical area of interest; a criterion determination module for allowing the user to determine a target outcome criterion; processing module for performing a comparison by comparing the first set of image data with a second set of image data corresponding to a post-treatment radiological study of the patient, the second set of image data including a treated clinical area of interest; and a criterion evaluation module for automatically evaluating the comparison to determine a post-treatment effect. In an embodiment, the criterion evaluation module is further for evaluating automatically a treatment effectiveness evaluation based on an extent to which the post-treatment effect satisfies the target outcome criterion.

20 Claims, 3 Drawing Sheets

AUTOMATIC OUTCOME ANALYSIS USING RADIOLOGICAL IMAGES

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present invention relate generally to analysis of radiological studies. Specifically, embodiments of the present invention relate to providing quantitative and visual analysis of pre and post treatment radiological studies.

Radiology imaging can be used to image a patient and a clinical area of interest before, and after a procedure. In order to determine whether the procedure is successful, the clinician (e.g., radiologist or treating physician) may visually compare the pre and post-treatment images. It may be difficult to quantitatively evaluate the outcomes of treatment by visual inspection alone. Clinicians may have desired outcomes, and they may be described in text or as notes on the pre-treatment radiological study. In addition to visual inspection, it may be helpful to provide a clinician with a quantitative and automatic evaluation of the success of a procedure. Thus, there is a need for quantitative and automatic evaluation of a procedure through radiological imaging.

BRIEF SUMMARY OF THE INVENTION

Certain embodiments of the present invention provide a system for analyzing a treatment of a patent including: an interactive image editor for allowing a user to interact with a first set image data corresponding to a pre-treatment radiological study of a patient, the first set of image data including an untreated clinical area of interest, such that the user is allowed to interact with the first set of image data to form a target outcome image for the clinical area of interest; a criterion determination module for allowing the user to determine a target outcome criterion; processing module for performing a comparison by comparing the target outcome image with a second set of image data corresponding to a post-treatment radiological study of the patient, the second set of image data including a treated clinical area of interest; and a criterion evaluation module for automatically evaluating the comparison to determine a post-treatment effect. In an embodiment, the criterion evaluation module is further for evaluating automatically a treatment effectiveness evaluation based on an extent to which the post-treatment effect satisfies the target outcome criterion. In an embodiment, the system further includes automatically reporting the treatment effectiveness evaluation to the user. In an embodiment, the system further includes a database for storing the pre-treatment radiological image, the post-treatment radiological image, the target outcome image, the target outcome criterion and the treatment effectiveness evaluation. In an embodiment, a subsequent user is allowed to form a report at least in part by retrieving a plurality of the target outcome criterion and a plurality of the treatment effectiveness evaluations from the database. In an embodiment, the system further includes a display module for displaying the treatment effectiveness evaluation. In an embodiment, the target outcome criterion includes a deviation.

Certain embodiments of the present invention provide a method for analyzing a treatment of a patent including: displaying a first set of image data corresponding to a pretreatment radiological study of a patient, the first set of image data including an untreated clinical area of interest; allowing a user to interact with the first set of image data to form a target outcome image for the clinical area of interest; allowing the user to determine a target outcome criterion; storing the target outcome image and the target outcome criterion; displaying a second set of image data corresponding to a post-treatment radiological study of the patient, the second set of image data including a treated clinical area of interest; retrieving the target outcome image and target outcome criterion; and comparing automatically the target outcome image with the second set of image data to determine a post-treatment effect. In an embodiment, the method further includes evaluating automatically a treatment effectiveness evaluation based on an extent to which the post-treatment effect satisfies the target outcome criterion. In an embodiment, the method further includes automatically reporting the treatment effectiveness evaluation to the user. In an embodiment, the method further includes storing in a library the pre-treatment radiological image, the post-treatment radiological image, the target outcome image, the target outcome criterion and the treatment effectiveness evaluation. In an embodiment, the method further includes retrieving a plurality of the target outcome criterion and a plurality of the treatment effectiveness evaluations to form a report. In an embodiment, the method further includes displaying the treatment effectiveness evaluation. In an embodiment, the target outcome criterion includes a deviation.

Certain embodiments of the present invention provide a non-transitory computer readable storage medium including a set of instructions for a computer, the set of instructions including: a first display routine for displaying a first set of image data corresponding to a pretreatment radiological study of a patient, the first set of image data including an untreated clinical area of interest; an interaction routine for allowing a user to interact with the first set of image data to form a target outcome image for the clinical area of interest; a determination routine for allowing the user to determine a target outcome criterion; a storage routine for storing the target outcome image and the target outcome criterion; a second display routine for displaying a second set of image data corresponding to a post-treatment radiological study of the patient, the second set of image data including a treated clinical area of interest; a retrieval routine for retrieving the target outcome image and target outcome criterion; and a comparison routine for comparing automatically the target outcome image with the second set of image data to determine a post-treatment effect. In an embodiment, the non-transitory computer readable storage medium including the set of instructions further includes an evaluation routine for evaluating automatically a treatment effectiveness evaluation based on an extent to which the post-treatment effect satisfies the target outcome criterion. In an embodiment, the non-transitory computer readable storage medium including the set of instructions further includes a reporting routine for automatically reporting the treatment effectiveness evaluation to the user. In an embodiment, the non-transitory computer readable storage medium including the set of instructions further includes a storage routine for storing in a library the pre-treatment radiological image, the post-treatment radiological image, the target outcome image, the target outcome criterion and the treatment effectiveness evaluation. In an embodiment, the non-transitory computer readable storage medium including the set of instructions further includes a retrieval routine for retrieving a plurality of the target outcome criterion and a plurality of the treatment effectiveness evaluations to form a report. In an embodiment, the target outcome criterion includes a deviation.

Figure 1:
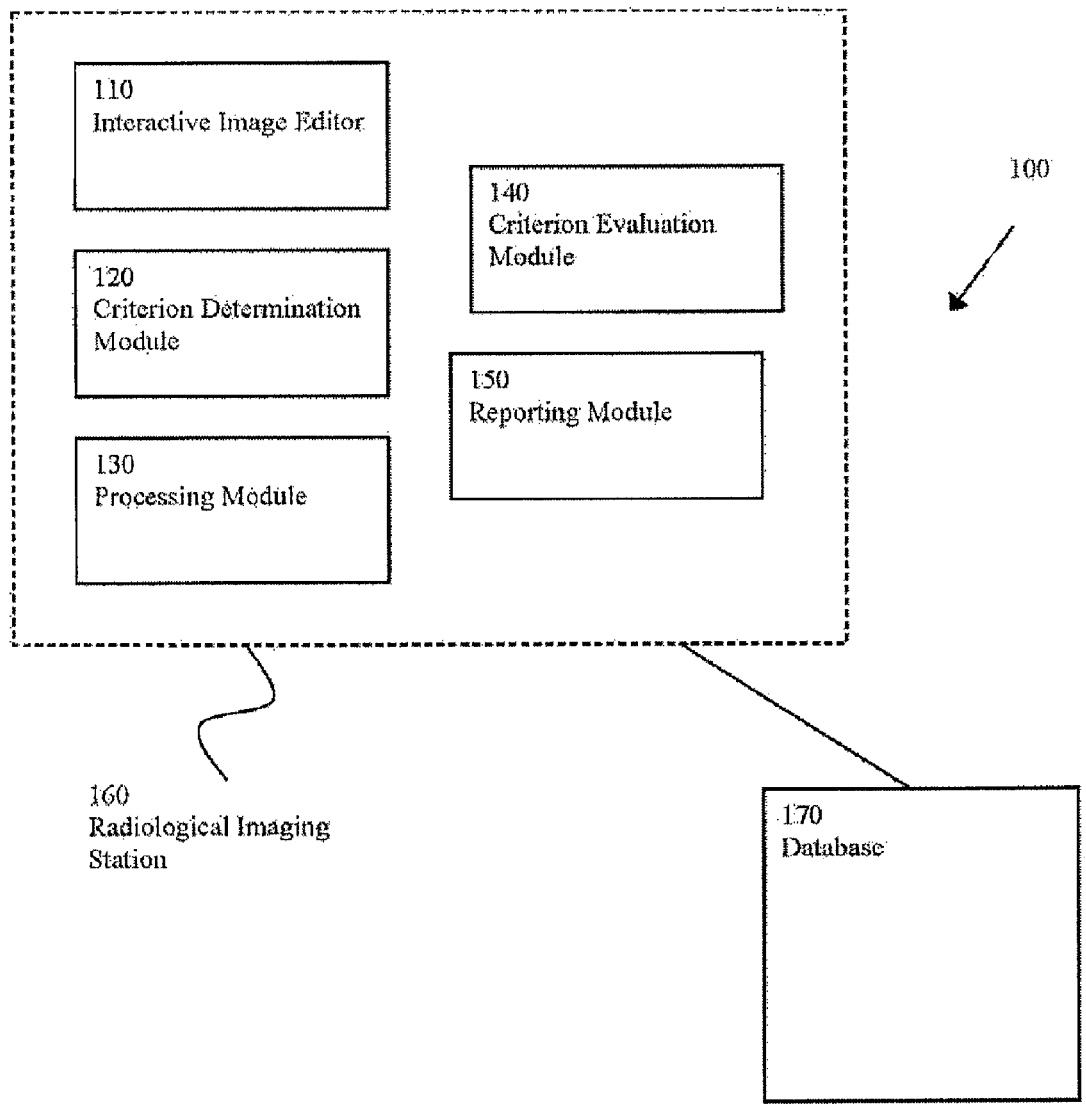
FIG. 1 shows a system for analyzing a treatment of a patient, in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 shows a block diagram 100 of a system for analyzing a treatment of a patient, in accordance with an embodiment of the present invention. System 100 includes an interactive image editor 110, a criterion determination module 120, a processing module 130, a criterion evaluation module 140, a reporting module 150, a radiological imaging station 160, and a database 170. One or more portions of system 100, such as radiological imaging station 160, may be incorporated into an enterprise system, such as a radiological information system ("RIS"), or picture archiving and communication system ("PACS"). The components may be centrally located, or may be distributed, for example, across a network. The components may be physical and/or logical. The components may be implemented as software or firmware, for example, by a computer readable storage medium having a set of instructions.

The interactive image editor 110 allows a user, such as a radiologist or other clinician, to interact with a first set of image data that corresponds to a pre-treatment radiological study of a patient. Image data that corresponds to a radiological study may be generated by a radiological imaging techniques, such as x-ray, CT scan, tomography, MRI, or ultrasound, for example. The image data may be 2D, 3D, or 4D. The first set of image data includes an untreated clinical area of interest. Note, that the untreated clinical area of interest may have been previously treated, but will be subject to additional treatment. A variety of interactive user controls, such as a mouse, keyboard, or touch-screen may allow the user to interact with the first set of image data. Through the interaction, the user can edit the first set of image data to form a target outcome image. For example, a user may interact with the first set of image data to create a desired outcome of a procedure, such as surgery.

The criterion determination module 120 allows the user to determine a target outcome criterion. Like the interactive image editor 110, the criterion determination module 120 may allow the user to interact with a variety of interactive user controls. The target outcome criterion can be a metric that quantifies a desired outcome of a procedure. For example, the target outcome criterion can be geometric information, such as a distance, an angle, a radius, etc. The user may be able to determine more than one target outcome criterion. For example, the user may determine a criterion that is related to geometric information, such as an acceptable deviation.

The processing module 130 compares a second set of image data with the first set of image data. The second set of image data corresponds to a post treatment radiological study of the patient. The second set of image data shows the treated clinical area of interest. The processing module 130 compares the first and second sets of image data. The criterion evaluation module 140 then may automatically evaluate the comparison to determine a post-treatment effect. The post-treatment effect may represent the extent to which the treatment achieved the target outcome criterion.

The processing module 130 and criterion evaluation module 140 may employ image processing algorithms to perform the comparison and evaluation, such as the diamond search algorithm and the variance comparison algorithm.

The reporting module 150 can generate a report corresponding to various data. For example, the reporting module can generate a report that reflects the post-treatment effect. This report may be automatically generated, and may be stored and/or transmitted to one or more interested parties, such as the treating clinician or radiologist. A database 170 may store one or more of the data sets, evaluations, comparisons, outcomes, and criterion discussed above.

Figure 2:
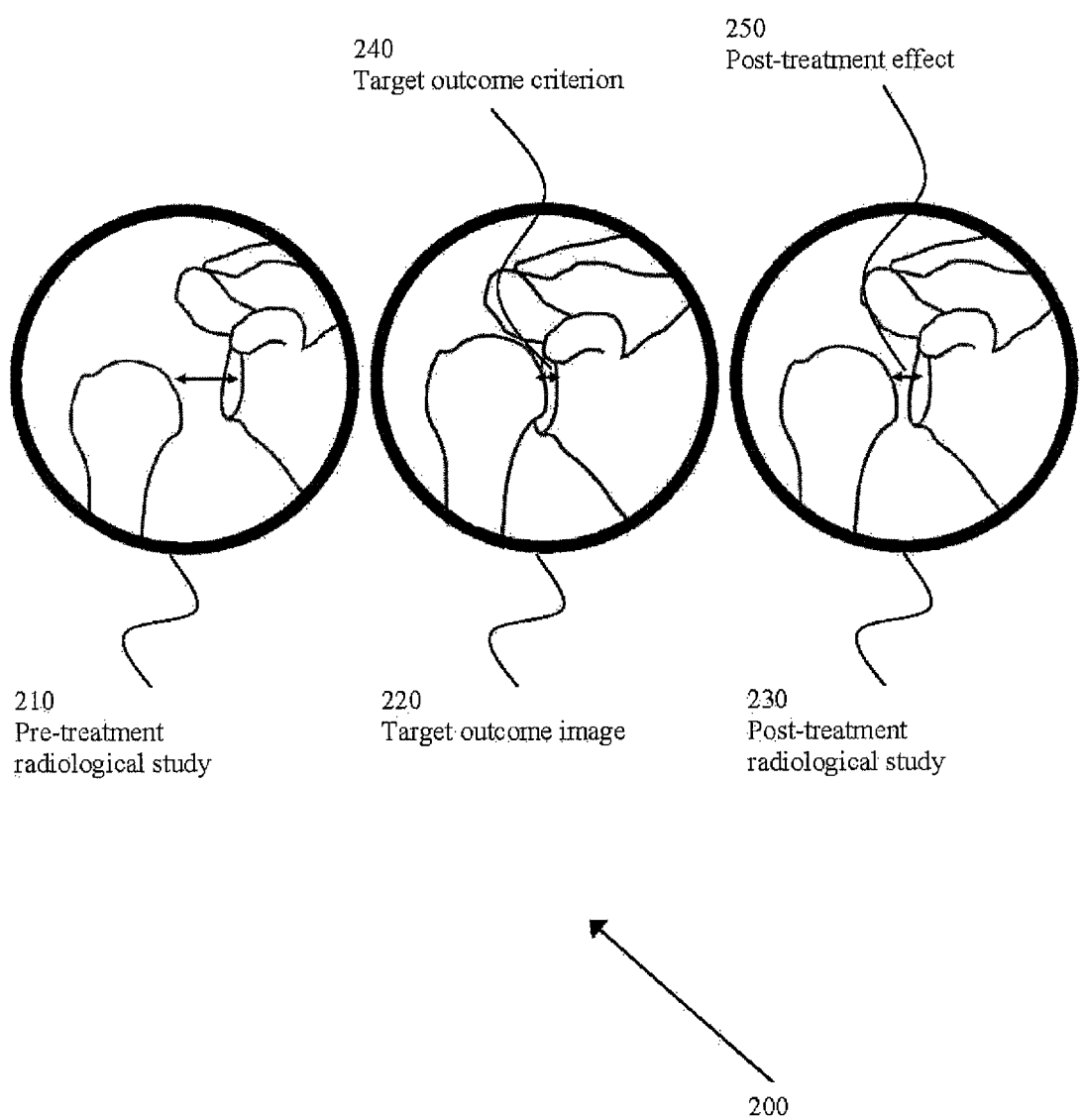
FIG. 2 shows an example of target outcome evaluation, in accordance with an embodiment of the present invention.

An illustrative example of the analysis of system 100 is shown in FIG. 2. A pre-treatment radiological study 210 shows a patient's dislocated shoulder. The pre-treatment clinical area of interest shows the patient's humerus head (shoulder ball) hanging outside his glenoid (shoulder socket). The orthopedic surgeon is planning a reduction surgery to replace the humerus head into the glenoid. A radiologist may view the pre-treatment radiological study 210, and edit the image to form a target outcome image 220. In the target outcome image, the radiologist has moved the humerus head into the glenoid. Such a configuration represents a desired outcome of the reduction surgery. The radiologist can also specify one or more target outcome criterion 240. In this example, the criterion 240 is the distance of the humerus head to the glenoid. After surgery, the patient's shoulder is imaged, and the post-treatment radiological study 230 is evaluated to determine the post-treatment effect 250. In this example, the post-treatment effect 250 is the post-treatment distance between the humerus head and the glenoid. The post-treatment effect 250 may then be compared or evaluated to the target outcome criterion 240 to determine whether the surgery was clinically successful.

Figure 3:
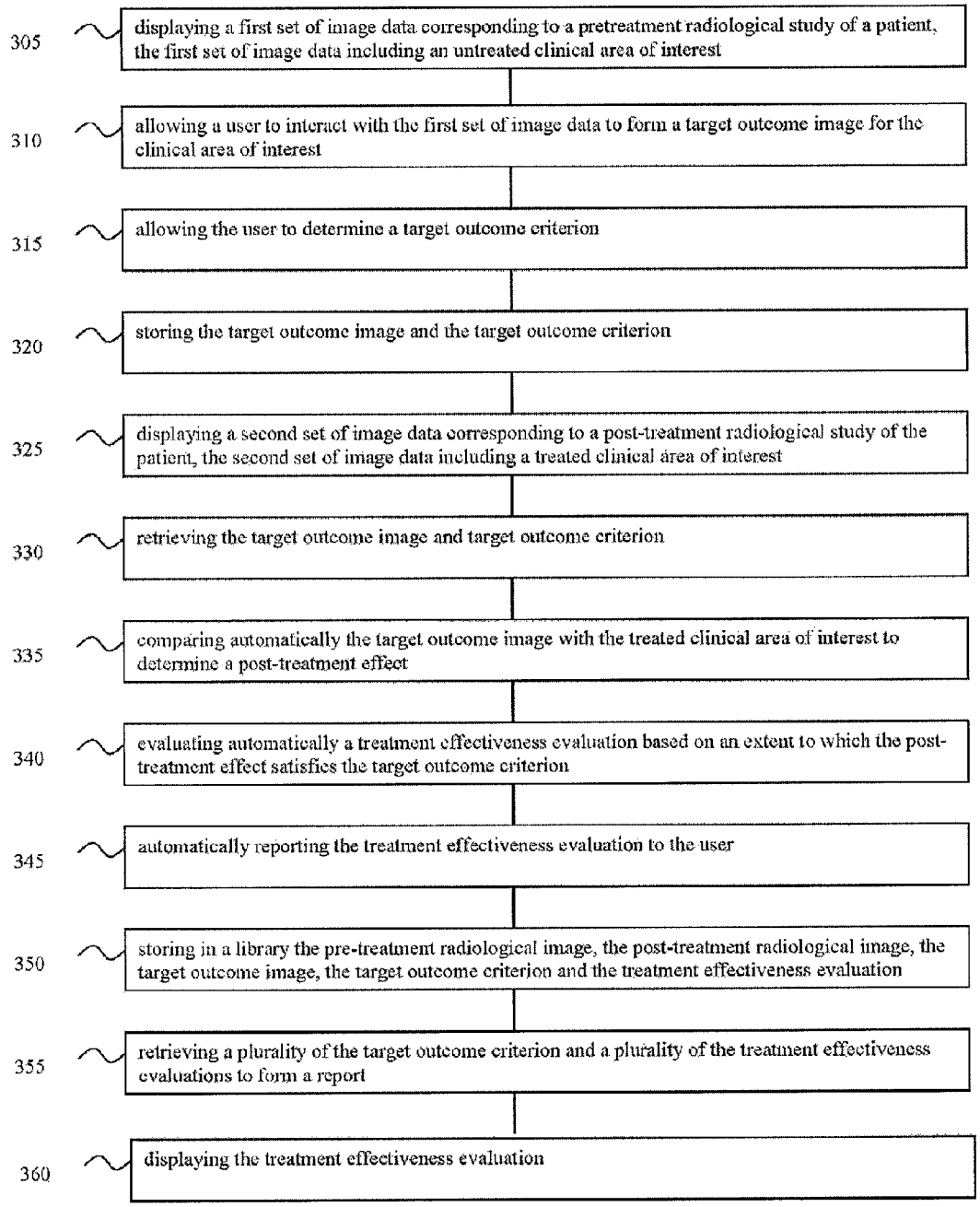
FIG. 3 shows a flowchart for a method of analyzing a treatment of a patient, in accordance with an embodiment of the present invention.

FIG. 3 shows a flow chart 300 for a method of analyzing a treatment of a patient, in accordance with an embodiment of the present invention. The steps of the flow chart 300 may be performable, for example, by a system, such as system 100. Furthermore, the steps of method 300 may be performable in a different order, or some steps may be omitted according to design and/or clinical preferences. For example, step 345 may be performed after step 350. Method 300, or a portion thereof, may be performable by one or more processing units. Method 300, or a portion thereof, may be performable by software, hardware, and/or firmware. Method 300, or a portion thereof, may also be expressible through a set of instructions stored on one of more computer-readable storage media, such as RAM, ROM, EPROM, EEPROM, optical disk, magnetic disk, magnetic tape, and/or the like.

At step 305, a first set of image data corresponding to a pretreatment radiological study of a patient is displayed. The first set of image data includes an untreated clinical area of interest. The first set of image data may be generated by a radiological imaging system in advance of a procedure. The data may be displayed on a radiological imaging station 160.

At step 310, a user is allowed to interact with the first set of image data to form a target outcome image with respect to the untreated clinical area of interest. The user may employ an interactive image editor 110 to manipulate the first set of image data. For example, as shown in FIG. 2, the user may move a bone. The user may move other bones, organs, or other anatomical structures. The user may also geometrically alter such structures, for example, by enlarging, reducing, or deforming them in the target outcome image.

At step 315, the user is allowed to determine a target outcome criterion for the clinical area of interest. The user may employ a criterion determination module 120 to determine the target outcome criterion. The target outcome criterion may be related to the target outcome image. For example, the target outcome criterion may be geometric data that relates to the desired target outcome. The user may assign a target outcome criterion based on the target outcome image, or independently. The target outcome criterion can be determined according to clinical preferences, and may include more than one parameter—such as a distance and an acceptable deviation.

At step 320, the target outcome image and target outcome criterion are stored, for example, in a storage such as database 170. At step 325, a second set of image data corresponding to a post-treatment radiological study of the patient is displayed. The second set of image data includes a treated clinical area of interest. The second set of image data may be generated by a radiological imaging system in advance of a procedure. The data may be displayed on a radiological imaging station 160. At step 330, target outcome image and target outcome criterion are retrieved from the storage (e.g., database 170).

At step 335, the target outcome image is compared with the treated clinical area of interest to determine a post-treatment effect. The comparison may be performed, for example, by the processing module 130. The comparison may identify differences between the two images, such as anatomical structures and/or the relationships therebetween. For example, the comparison may identify that, in the treated clinical area of interest, two bones are closer or farther apart than the target outcome image. This comparison may result in the determination of a post-treatment effect. At step 340 a treatment effectiveness evaluation is automatically evaluated based on the extent to which post-treatment effect satisfies the target outcome criterion. For example, the target outcome criterion may be a distance and a deviation. The post-treatment effect may be a distance. If the post-treatment effect distance is within the distance/deviation of the target outcome criterion, then the treatment effectiveness evaluation may be quantified to be successful. As another option, the treatment effectiveness may be a quantified metric that gauges the degree of success of the procedure.

At step 345 the treatment effectiveness evaluation is automatically reported to the user. For example, the user may be emailed, or otherwise alerted the success/failure or degree thereof for the completed procedure. At step 350 the pre-treatment radiological image, post-treatment radiological image, target outcome image, target outcome criterion and treatment effectiveness evaluation are stored in a library. The library may be stored, for example, in the database 170. The library may be logically or physically linked. At step 355 a report may be formed by retrieving a plurality of target outcome criterion and a plurality of corresponding treatment effectiveness evaluations. In this way, the data in the library can be mined in the future by clinicians or researchers. At step 360 the treatment effectiveness evaluation is displayed to the user, for example, on a workstation 160.

To illustrate an example, the flow chart 300 may be implemented in the following manner. Using the example provided in FIG. 2, a patient dislocated his shoulder, and a reduction surgery is planned. An x-ray image of the shoulder is performed before the surgery. The flow chart starts at step 305 by displaying the pre-treatment radiological study image 210 on the workstation 160. The pre-treatment radiological study image 210 contains a clinical area of interest—namely the dislocated humerus and glenoid. At step 310, a radiologist interacts through the interactive image editor 110 to edit the pre-treatment radiological study image 210. The radiologist moves the humerus towards the glenoid to show the ideal clinical outcome of the reduction surgery. As a result of the editing, a target outcome image 220 is generated. At step 315, the radiologist employs the criterion determination module to determine a target outcome criterion 240—namely that the humerus should be less than 5 mm from the glenoid, and that an acceptable deviation from this distance would be ±10% (or 4.5-5.5 mm). In this case, the radiologist draws a line between the ideal locations of the humerus and glenoid to calculate the distance. At step 320, the target outcome criterion 240, as well as the target outcome image 220 are stored in the database 170. Further, the target outcome image and criterion are also shown to the patient to educate him on the procedure and desired results.

Subsequently, the reduction surgery is performed on the patient. Then, the patient's shoulder is x-rayed to generate a post-treatment radiological study 230 of the shoulder area. At step 325, the post-treatment study 230 is displayed, again on the imaging station 160. At step 330, the prior target outcome image and criterion are retrieved from the database 170. At step 335, the target outcome image and the post-treatment radiological study 230 are automatically compared by the processing module 130. The comparison results in a post-treatment effect 250—namely that after the procedure, the humerus and glenoid are 4.8 mm apart. At step 340, the procedure is deemed to be successful because the post-treatment effect 250 is within the target outcome criteria—i.e. 4.5-5.5 mm. The success of the procedure, along with links to the images, effects, and criterion, are automatically reported to the radiologist and treating physician at step 345. At step 350, the pre-treatment radiological image, the post-treatment radiological image, the target outcome image, the target outcome criterion, and the treatment effectiveness evaluation are stored together in the database 170. Some of these files may have been previously stored at step 320. At step 360, the treatment effectiveness evaluation is displayed to the radiologist and treating physician. The clinicians, thus, can also evaluate the success of the procedure visually, as well as share the good news and images with the patient.

Years later, a researcher wants to gather data on reduction surgeries. At step 355, treatment effectiveness evaluations and corresponding target outcome criteria are retrieved from the database, and a report is generated for research purposes.

Thus, embodiments of the present invention provide for quantitative and automatic evaluation of a procedure through radiological imaging.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A system for analyzing a treatment of a patent comprising:
   an interactive image editor for allowing a user to interact with a first set image data corresponding to a pre-treatment radiological study of a patient, said first set of image data comprising an untreated clinical area of interest, such that said user is allowed to interact with said first set of image data to form a target outcome image for said clinical area of interest;
   a criterion determination module for allowing said user to determine a target outcome criterion;
   a processing module for performing a comparison by comparing said target outcome image with a second set of image data corresponding to a post-treatment radiological study of said patient, said second set of image data comprising a treated clinical area of interest; and
   a criterion evaluation module for automatically evaluating said comparison to determine a post-treatment effect.

2. The system of claim 1 wherein said criterion evaluation module is further for evaluating automatically a treatment effectiveness evaluation based on an extent to which said post-treatment effect satisfies said target outcome criterion.

3. The system of claim 2 further comprising automatically reporting said treatment effectiveness evaluation to said user.

4. The system of claim 1 further comprising a database for storing said pre- treatment radiological image, said post-treatment radiological image, said target outcome image, said target outcome criterion and said treatment effectiveness evaluation.

5. The system of claim 4, wherein a subsequent user is allowed to form a report at least in part by retrieving a plurality of said target outcome criterion and a plurality of said treatment effectiveness evaluations from said database.

6. The system of claim 2 further comprising a display module for displaying said treatment effectiveness evaluation.

7. The system of claim 1, wherein said target outcome criterion comprises a deviation.

8. A method for analyzing a treatment of a patent comprising:
   displaying a first set of image data corresponding to a pretreatment radiological study of a patient, said first set of image data comprising an untreated clinical area of interest;
   allowing a user to interact with said first set of image data to form a target outcome image for said clinical area of interest;
   allowing said user to determine a target outcome criterion;
   storing said target outcome image and said target outcome criterion;
   displaying a second set of image data corresponding to a post-treatment radiological study of said patient, said second set of image data comprising a treated clinical area of interest;
   retrieving said target outcome image and target outcome criterion; and
   comparing automatically said target outcome image with said second set of image data to determine a post-treatment effect.

9. The method of claim 8 further comprising evaluating automatically a treatment effectiveness evaluation based on an extent to which said post-treatment effect satisfies said target outcome criterion.

10. The method of claim 9 further comprising automatically reporting said treatment effectiveness evaluation to said user.

11. The method of claim 9 further comprising storing in a library said pre-treatment radiological image, said post-treatment radiological image, said target outcome image, said target outcome criterion and said treatment effectiveness evaluation.

12. The method of claim 11 further comprising retrieving a plurality of said target outcome criterion and a plurality of said treatment effectiveness evaluations to form a report.

13. The method of claim 9 further comprising displaying said treatment effectiveness evaluation.

14. The method of claim 8, wherein said target outcome criterion comprises a deviation.

15. A non-transitory computer readable storage medium including a set of instructions for a computer, the set of instructions comprising:
   a first display routine for displaying a first set of image data corresponding to a pretreatment radiological study of a patient, said first set of image data comprising an untreated clinical area of interest;
   an interaction routine for allowing a user to interact with said first set of image data to form a target outcome image for said clinical area of interest;
   a determination routine for allowing said user to determine a target outcome criterion;
   a storage routine for storing said target outcome image and said target outcome criterion;
   a second display routine for displaying a second set of image data corresponding to a post-treatment radiological study of said patient, said second set of image data comprising a treated clinical area of interest;
   a retrieval routine for retrieving said target outcome image and target outcome criterion; and
   a comparison routine for comparing automatically said target outcome image with said second set of image data to determine a post-treatment effect.

16. The non-transitory computer readable storage medium including the set of instructions of claim 15 further comprising an evaluation routine for evaluating automatically a treatment effectiveness evaluation based on an extent to which said post-treatment effect satisfies said target outcome criterion.

17. The non-transitory computer readable storage medium including the set of instructions of claim 16 further comprising a reporting routine for automatically reporting said treatment effectiveness evaluation to said user.

18. The non-transitory computer readable storage medium including the set of instructions of claim 16 further comprising a storage routine for storing in a library said pre-treatment radiological image, said post-treatment radiological image, said target outcome image, said target outcome criterion and said treatment effectiveness evaluation.

19. The non-transitory computer readable storage medium including the set of instructions of claim 18 further comprising a retrieval routine for retrieving a plurality of said target outcome criterion and a plurality of said treatment effectiveness evaluations to form a report.

20. The non-transitory computer readable storage medium including the set of instructions of claim 15, wherein said target outcome criterion comprises a deviation.

* * * * *